(12) United States Patent
Vilkomerson (10) Patent No.: US 9,681,853 B2
(45) Date of Patent: *Jun. 20, 2017

(54) FLOW MEASUREMENT APPARATUS AND METHOD

(71) Applicant: DVX, LLC, Princeton, NJ (US)

(72) Inventor: David Vilkomerson, Princeton, NJ (US)

(73) Assignee: DVX, LLC, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/475,541

(22) Filed: Sep. 2, 2014

(65) Prior Publication Data

US 2014/0371595 A1    Dec. 18, 2014

Related U.S. Application Data

(63) Continuation-in-part of application No. 13/358,507, filed on Jan. 25, 2012, now Pat. No. 8,852,110.

(60) Provisional application No. 61/437,945, filed on Jan. 31, 2011.

(51) Int. Cl.
| A61B 8/00 | (2006.01) |
| A61B 8/08 | (2006.01) |
| A61B 8/06 | (2006.01) |
| G01F 1/66 | (2006.01) |

(52) U.S. Cl.
CPC ............ *A61B 8/488* (2013.01); *A61B 8/06* (2013.01); *A61B 8/4455* (2013.01); *A61B 8/4483* (2013.01); *A61B 8/0891* (2013.01); *A61B 8/4494* (2013.01); *G01F 1/663* (2013.01)

(58) Field of Classification Search
None
See application file for complete search history.

(56) References Cited

U.S. PATENT DOCUMENTS

| 5,488,953 A | 2/1996 | Vilkomerson |
| 5,540,230 A | 7/1996 | Vilkomerson |
| 5,713,362 A | 2/1998 | Vilkomerson |
| 2005/0070799 A1* | 3/2005 | Vilkomerson et al. ....... 600/454 |

(Continued)

OTHER PUBLICATIONS

Macefield et etl. ("Firing properties of single vasoconstrictor neurones in human subjects with high levels of muscle sympathetic activit"; Journal of PHysiology (1999), 516.1, pp. 293-301).*

(Continued)

*Primary Examiner* — Amanda Lauritzen Moher
*Assistant Examiner* — Shahdeep Mohammed
(74) *Attorney, Agent, or Firm* — Fox Rothschild LLP (57) ABSTRACT

The velocity of fluids containing particles that scatter ultrasound can be measured by determining the Doppler shift of the ultrasound scattered by the particles in the fluid. Measuring fluid flow in cylindrical vessels such as blood vessels is an important use of Doppler ultrasound. This invention teaches using various configurations of cylindrical diffraction-grating transducers and cylindrical non-diffraction-grating transducers that suppress the Doppler shift from non-axial components of fluid velocity while being sensitive to the Doppler shift produced by axial velocity components. These configurations thus provide accurate measurement of the net flow down the vessel, even when the fluid flow is curved or not parallel to the vessel wall.

18 Claims, 7 Drawing Sheets

(56) References Cited

U.S. PATENT DOCUMENTS

2007/0119239 A1* 5/2007 Priev .................... G01N 15/06
73/61.75
2008/0139940 A1* 6/2008 Vilkomerson et al. ....... 600/454

OTHER PUBLICATIONS

Wang et al. ("Nucleoside-Derived antagonists to A3 adenosine receptor lower mouse intracular pressure and act across species"; Experimental Eye research (2010, pp. 146-154).*
Chapter 6, Signal Detection and Pre-processing: CW and PW Doppler, in "Doppler Ultrasound" by Evans and McDicken, 2nd Ed, J. Wiley and Sons, New York 2000.
Chapter 12, Volumetric Blood Flow Measurement, in "Doppler Ultrasound" by Evans and McDicken, 2nd Ed, J. Wiley and Sons, New York 2000.
Treeby BE, Zhang EZ, Thomas A, Cox B, Measurement of the Ultrasound Attenuation and Dispersion in Whole Human Blood and Its Components from 0-70 MHz, Ultrasound in Medicine and Biology 2011;37:289-300.
Cannata et al, "A Flexible Implantable Sensor for Postoperative Monitoring of Blood Flow", presentation at the 2010 Annual Meeting of the American Institute of Ultrasound in Medicine, Mar. 2010.
Robert T. Beyer, "From Sounds of Our Times: Two Hundred Years of Acoustics", Springer-Verlag New York, 1999, p. 88.

* cited by examiner

FLOW MEASUREMENT APPARATUS AND METHOD

CROSS-REFERENCE TO RELATED APPLICATIONS

This application is a continuation-in-part of U.S. application Ser. No. 13/358,507, filed on Jan. 25, 2012, which also claims the benefit of U.S. Provisional Application Ser. No. 61/437,945, filed on Jan. 31, 2011, both hereby incorporated by reference.

REFERENCE TO GOVERNMENT FUNDING

This application was made with partial Government support under contract 2R44HL071359 awarded by the NHLBI of the National Institute of Health. The Government has certain rights in this invention.

FIELD OF THE INVENTION

The present invention generally relates to flow measurement and more particularly to measurement of velocity of fluid containing ultrasound scatterers flowing through a pipe or blood vessel using Doppler techniques.

BACKGROUND OF THE INVENTION

As the function of a pipe is to carry a volume of fluid from one point to another, the flow volume passing through it determines how well it is functioning. We will refer to fluid-carrying pipes as "vessels", as in an exemplary application of measurement of flow in blood vessels. However, the teaching of how to measure flow volume in the present invention is applicable to measurement of flow of any liquid that contains particles that scatter ultrasound, e.g. milk, slurries, water containing bubbles, etc, as well as blood. Using ultrasound Doppler techniques to measure the flow of blood is well known. Red blood cells act as scatterers of ultrasound in the MHz frequency region, and when they are insonated by a beam of ultrasound their movement creates a Doppler shift in the scattered sound. The amount of shift in frequency, also known as the Doppler shift, is proportional to the number of wavelengths of ultrasound per second that the red blood cell moves. This proportionality is the cosine of the angle between the velocity of the scatterer and the direction of propagation of the ultrasound beam. As the peak velocity of blood in human blood vessels is about 1 meter/second, using ultrasound in the low MHz, where the wavelength is a fraction of a millimeter, leads to Doppler shifts in the low KHz, i.e. in the audible region, in which detected signals can be heard. By detecting the Doppler shifts, the velocity of the blood cells can be calculated. See, for example "Doppler Ultrasound" by Evans and McDicken, $2^{nd}$ Ed, J. Wiley and Sons, New York 2000, for a thorough discussion of the use of Doppler ultrasound in measuring blood velocity.

Doppler velocity measurements are usually made with a combination of an image of the vessel with a graphic presentation of the Doppler shift vs time, known as "duplex Doppler". The translation of the measured Doppler shift to the more useful velocity generally assumes the flow to be parallel to the axis of the vessel. Other techniques that have been proposed require multiple frequencies or complex mathematical manipulations of the signal. Conventional ultrasound methods often sample only a small portion of the flow through a vessel and extrapolate a flow from that small sample. This, however, frequently causes measurement to be inaccurate.

The present invention provides an apparatus and method to overcome these drawbacks in the existing Doppler measurement art. In the present invention, we teach a new configuration for direct application to the vessel to allow accurate measurement of flow carried by the vessel. Because rotational symmetric cylindrical transducers are used, this configuration will produce Doppler signals only from the flow directions down the tube, i.e. parallel to the axis; these flow components are the ones which are significant for determining the volume actually conveyed by the vessel. Moreover, unlike conventional ultrasound methods that sample only a small portion of the flow through a vessel and extrapolate a flow volume from that small sample, the present invention measures flow through most of the cross-section of the lumen, thus can provide an accurate measurement.

SUMMARY OF THE INVENTION

Figure 1:
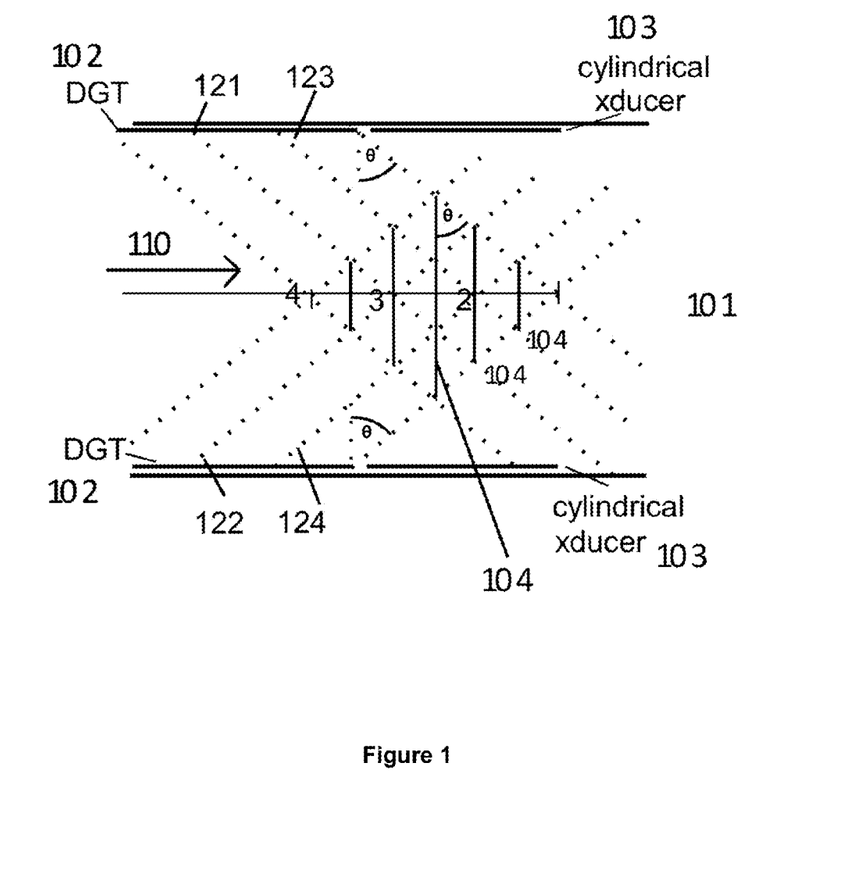
FIG. 1 shows the cross-section of the basic configuration, the combination of a cylindrical DGT with a cylindrical non-DGT transducer according to one aspect of the present invention.

The present invention uses a new configuration of transducers, a combination of a cylindrical DGT (or diffraction-grating transducer) and a cylindrical non-diffraction-grating transducer (or non-DGT). As will be seen, these cylindrical transducers provide special characteristics that produce the improved operation over non-cylindrical transducers. FIG. 1 shows the configuration in side view, i.e. a slice through the tube 101 along its axis. The wavefronts launched by the cylindrical DGT 102 on opposite walls of the vessel produces planes of "standing waves", i.e. equiphase plane as expressed by lines 104, perpendicular to the vessel axis. A moving scattering particle, e.g. a red blood cell, with component of velocity along the axis, scatters a signal of changing phase as it crosses the different equiphase planes; the scattered ultrasound is received by the cylindrical transducer 103. The scattered signal has a changing phase with respect to the driving signal on the DGT, i.e. a Doppler shift in the received signal compared to the transmitting frequency. Any velocity component perpendicular to the axis of the vessel is parallel to the equiphase planes 104, and will scatter only a constant-phase replica of the transmitted signal, producing a signal with zero Doppler shift from the cylindrical transducer.

Both DGT and non-DGT transducer are rotationally symmetric, i.e. completely wrapped around the lumen or substantially (nearly complete) wrapped around the lumen, so in a complete vessel equiphase planes are formed, rather than equiphase lines. Therefore in those regions Doppler shifts arise only from the axial component of velocity and do not arise from any non-axial components.

As it is only the axial component of velocity that produces flow through a vessel, the Doppler signal produced by this configuration accurately measures the flow down the vessel, and, unlike conventional configurations, is not affected by non-axial flow and therefore gives more accurate results.

According to one aspect of the present invention, a configuration of a cylindrical DGT next to a cylindrical non-DGT is used so that only velocity that is along the direction of the cylinder's axis, which is proportional to the flow direction 110 (in FIG. 1), generates a Doppler signal. This is the unique contribution of using cylindrical DGT with a cylindrical non-DGT.

Figure 8:
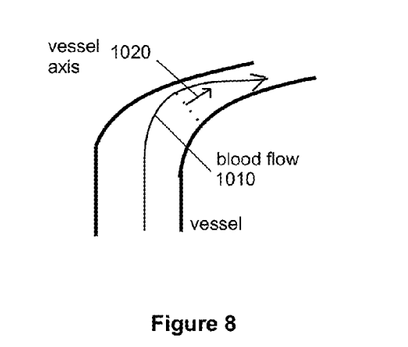
FIG. 8 shows how curved blood vessels produce blood velocity vectors non-parallel to the vessel axis.

With reference to FIG. 8, in a typical curved human blood vessel, the direction of blood flow (1010) is not parallel to the axis of the vessel (1020). Because the vessel is a cylindrically symmetric structure, the particle velocity can be resolved into axial and perpendicular vector components, and it is only the velocity along the axis that contributes to volume flow. Therefore, the present invention is advantageous over existing Doppler ultrasound means of measuring flow such that it can provide accurate measurement of flow when the velocity is not parallel to the vessel wall.

The Doppler frequency generated by a scatterer is proportional to its velocity, and different scatterers may move at different velocities, mostly with scatterers near the center of the vessel moving at higher velocity than the scatterers near the wall. It is a well-known technique, as taught by Evans and McDicken in Chapter 12, Volumetric Blood Flow Measurement, in "Doppler Ultrasound", $2^{nd}$ Ed, J. Wiley and Sons, New York 2000, that the total flow can be calculated from the spectrum of the Doppler signal by recognizing that the amount of power at each frequency bin of the Doppler spectrum represents the number of scatterers moving at the corresponding velocity; summing the Doppler power corresponding to each velocity therefore gives the total flow volume. The configuration according to the present invention insonates almost the entire lumen so all parts of the vessel's flow contribute to the measurement of flow.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

With reference to FIG. 1, cylindrical DGT 102 establishes equiphase planes 104. The DGT 102 produces a beam at an angle of $\theta$, with respect to the perpendicular to the vessel axis 110, where $\sin \theta = \lambda/d$, where $\lambda$ is the wavelength of the ultrasound in blood at the frequency used, and d is the periodicity, i.e. the distance between points of equal phase, of the grating of the DGT. The wavefronts from the opposite walls of the vessel will cross, producing a standing wave pattern. For example, the wavefront coming from the top DGT 121 will intersect with the wavefront launched at the same time (i.e. same phase) at the corresponding point at the bottom of the vessel 122, and those wavefronts must be in phase where they intersect, producing an equiphase front. Similarly, the next corresponding points 123 and 124 on the DGT will intersect at the next equiphase front, etc.

Figure 2A:
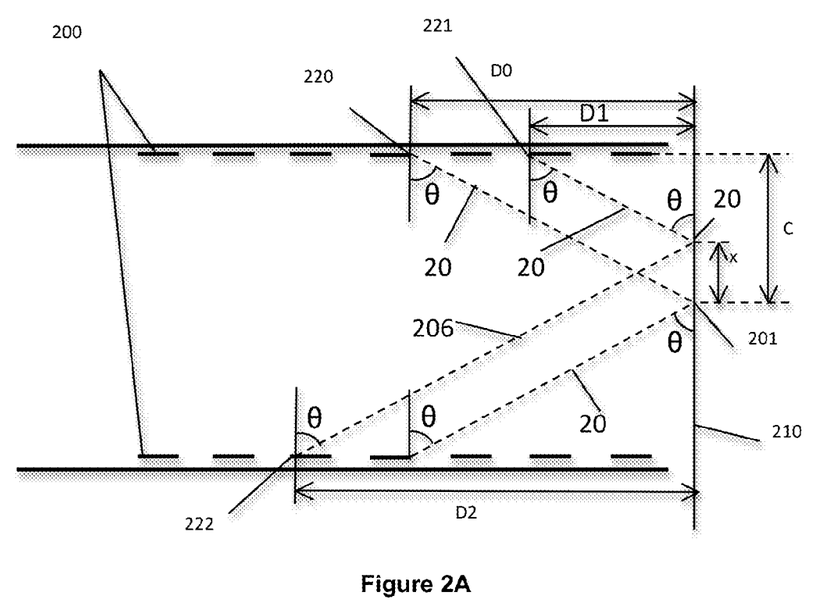
FIG. 2A and FIG. 2B show the wavefronts arising from the interaction of the waves launched from opposite sides of the vessel by the cylindrical DGT according to one aspect of the present invention.

With reference to FIG. 2A, in a cylindrical DGT 200, if we take a central electrode of the transducer at 220, the propagating path 205 from the top is the same length as propagating path 204, from the bottom of the transducer. Where they intersect, at 201 (at equal distance C from the top or bottom wall of the vessel), on the plane 210, they have the same phase, as they were launched from the same element and traveled the same distance to reach 201.

If we now consider a new point on the plane 210 a distance x away, at 202, we see that there is a path 207 from 221 on the upper part of the transducer that intersects at point 202 with a path 206 from point 222.

The lengths of the paths 207 and 206 are different. However, we can show that the change in phase in the two paths 206 and 207 when moving from the equal-length intersection point 201 to the arbitrary point 202 cancel, i.e. the increase in path length of one path is exactly the same as the decrease in path length of the other, so the net change in phase of the intersection point 202 is zero. As the distance x is arbitrary, this shows all points on that plane 210 have the same phase, i.e. it is an equiphase plane. This can be illustrated as below.

The propagating paths are always at an angle of $\theta$ to the perpendicular, determined by the spacing of the electrode elements. With reference to FIG. 2A, we can see that $\tan \theta = D1/(C-x) = D2/(C+x)$ where D1 is distance from plane 210 to the point where propagating path 207 begins, D2 is distance from plane 210 to the point where propagating path 206 begins, and D0 is the distance from plane 210 to the point where propagating path 205 and 204 begin. We can state $$D1 = (C-x)\tan \theta \text{ and } D2 = (C+x)\tan \theta. \ D0 = C \tan \theta, \text{ so}$$
$$D2 - D0 = x \tan \theta \text{ and } D0 - D1 = x \tan \theta$$

i.e. the originating point D1 along DGT 200 for propagating path 207 is the same distance from D0 toward the right as the originating point D2 for propagating path 206 is from the left and away the right for the other, are equal. As the phase along a DGT is continuously increasing, every d increasing by $2\pi$, that means the change in phase for one path is increasing by the same amount as the other is decreasing; therefore the net change in phase for the sum of the two paths 206 and 207 will always remain the same as the phase at point C, for arbitrary distance x or for any angle $\theta$. Hence, the plane 210 is an equiphase plane. Hence, a scattering particle moving along these planes will always scatter the same phase, i.e. will not produce a Doppler frequency shift. A particle moving perpendicular to these planes will cross the equiphase planes and scatter phase-shifted ultrasound, producing a change in the phase of the scattered signal, a Doppler frequency. Hence, velocity along the axis will produce a Doppler shift, velocity perpendicular to the axis will produce none, as desired for measuring flow through the vessel.

Figure 2B:
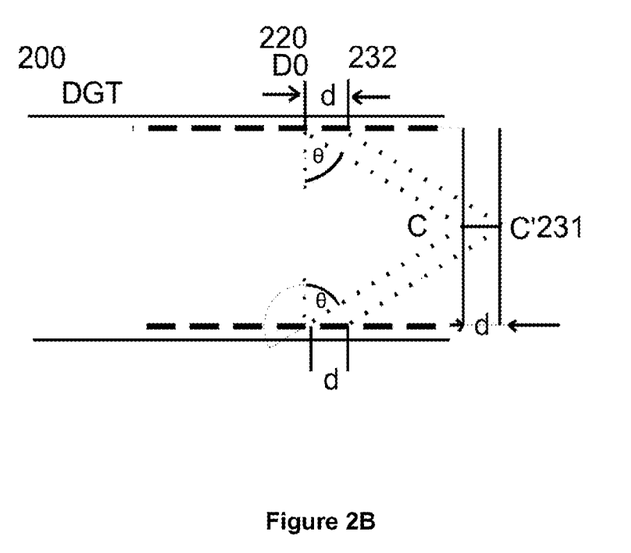

The amount of change in phase with velocity can be determined by determining the change in phase between equiphase planes. With reference to FIG. 2B, a new set of propagating paths to a new central point 231 is shown. By the characteristic of parallel lines that the distance at the same angle between two parallel lines must be the same, advancing a distance d, i.e. the periodicity of the DGT from 220 to 232, must advance the equiphase planes by the same distance, d, as shown.

The number of planes per unit of time $\Delta t$ that a particle moving along the axis crosses is expressed by $Np=D/d$, where D is the distance the particle travels, and d is the distance between these equiphase fronts, also the periodicity of the DGT. Because "$D$"=$v\Delta t$, $Np=D/d=v\Delta t/d$. The Doppler shift $f_p$ is expressed as the change of phase with time, which is the definition of radian frequency. Therefore, $f_D=\Delta\theta/\Delta t=\omega=2\pi\ Np/\Delta t=v/d$. Therefore, the Doppler signal frequency is proportional only to the velocity along the axis of the vessel (where the phase is changing); as volume-flow is proportional to only the velocity along the axis, this configuration is superior in accurately measuring volume-flow, an important advantage of the present invention.

Embodiment 1

While there are various methods of constructing ultrasonic transducers, in one exemplary method, DGT and non-DGT are constructed using a piezoelectric plastic transducer material, such as P(VDF-TrFE) coated on an electroded flexible plastic substrate such as polyimide film of 1-mil thickness. The electrodes for a DGT are placed such that their phase will advance $2\pi$ every d for the desired beam angle $\theta$ photolithographically applied. In this exemplary embodiment, with reference to FIG. 3A and FIG. 3B, a beam can be produced by the DGT at an angle of $\sin\theta=\lambda/d$. As is taught in U.S. Pat. Nos. 5,488,953 and 5,540,230, both to Vilkomerson, when four elements driven in phase advancement of $\pi/2$ make up one period separated by d/4, a single beam at this angle is produced. When 2 elements, separated by d/2 and driven at 180° are used, two symmetrical beams are produced. These patents are incorporated by reference.

Figure 3A:
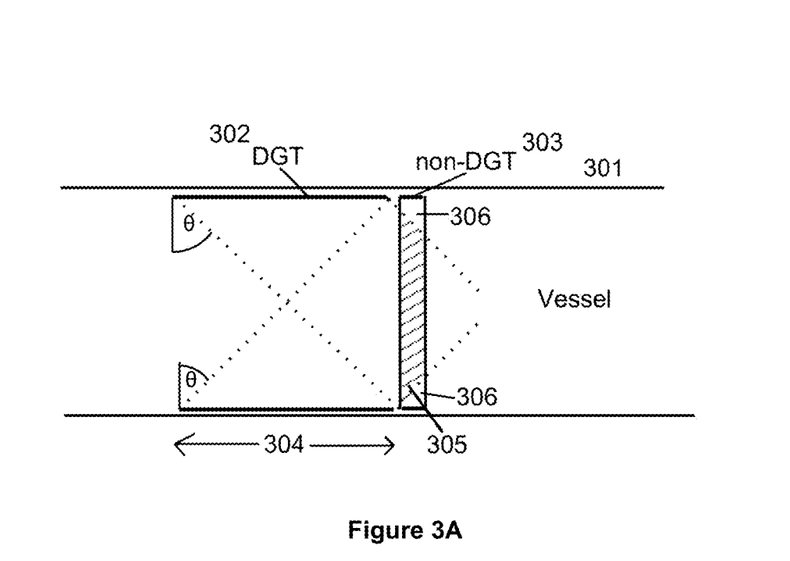
FIG. 3A and FIG. 3B show one embodiment according to one aspect of the present invention.
Figure 3B:
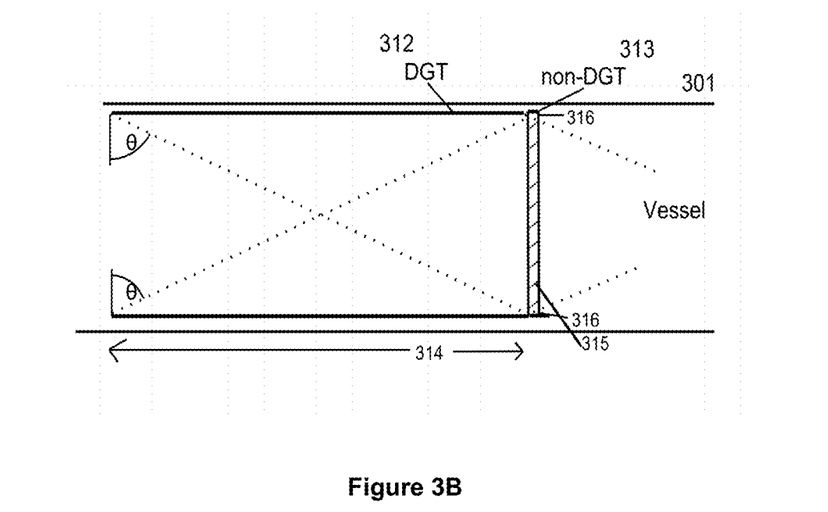
Figure 9A:
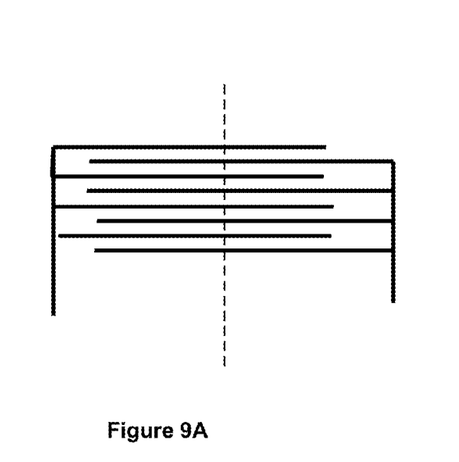
FIG. 9A and FIG. 9B show the forming of a cylindrical DGT by rolling up a double-beam DGT along an axis according to one aspect of the present invention.
Figure 9B:
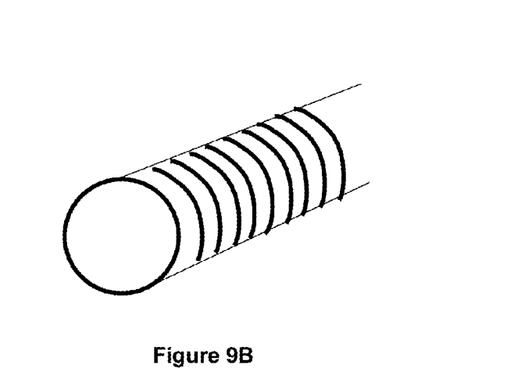

The film transducer can be wrapped outside or inside of a vessel or pipe. An exemplary structure, as shown in FIG. 9A and FIG. 9B, is first fabricated on a flat film and then wrapped around a vessel. With reference to FIG. 3A and FIG. 3B, a film transducer that is wrapped inside a vessel is shown. Those skilled in the art recognize that signal cables (not shown) will be required to drive the DGT, and to carry the received signal from the non-DGT cylindrical transducer. The cables can be coax, stripline or other types readily available on the market.

According to one aspect of the present invention, the plastic substrate is spin-coated with a piezoplastic layer such as 15 micron layer of P(VDF-TrFE) which in turn is sputter-coated with a conductor layer and the piezoplastic poled. The conductor layer is also used for producing the electric field needed for transducer operation. Construction of such flexible film DGT's were described in "A Flexible Implantable Sensor for Postoperative Monitoring of Blood Flow" by Cannata et al presented at the Annual Meeting of the American Institute of Ultrasound in Medicine, San Diego, Mar. 28, 2010.

Once the Doppler signal is obtained, it is processed in the usual manner of continuous wave (known as CW, in distinction from PW, pulsed wave Doppler that utilizes pulses of insonating ultrasound) Doppler e.g. Chapter 6. Signal Detection and Preprocessing, in "Doppler Ultrasound" by Evans and McDicken, $2^{nd}$ Ed, J. Wiley and Sons, New York 2000 to determine the velocity components and the flow.

If the velocity of the red blood cell is 1000 mm/sec (a velocity of blood found in the body) and d, the periodicity of the DGT, is 100 microns, the Doppler shift will be 1000/0.1=10 kHz. Similarly, given periodicity of the DGT and measurement of Doppler shift, the velocity can be determined from the relationship above, $v=d*f_D$.

Assuming a 6 mm diameter blood vessel is to be measured, for example, we use a 30 MHz ultrasound frequency. This frequency is chosen to produce a strong Doppler signal, as the amount of scattering of ultrasound increases by a factor of the frequency to the fourth power, while making the dimensions of the diffracting grating not so small as it is difficult to fabricate. The ultrasound wavelength at this frequency in blood is ~50 microns. Using a 45° beam, as shown in FIG. 3A, and using $\sin\theta=\lambda/d$, $\lambda/d=0.707$, so the periodicity d is set as 50/0.707=71 microns. The total center-to-center spacing (for four-element configuration) is therefore (71)/4=17.75. To enable poling the transducer elements, there must be sufficient space between the electrodes, but to provide enough active area, the electrode should not be too thin. Generally, roughly equal width to separation between the electrodes is used. According to one aspect of the present invention, the electrodes are made 10 microns wide for simplicity in fabrication, and the space between the electrodes becomes 7.75 microns wide. With reference to FIG. 3A, the length of the DGT 304 can be designed to be the same as the diameter, 6 mm, so the 45° beam from one edge of the DGT reaches the bottom of the vessel at the base of the non-DGT cylindrical transducer.

Note, as shown all of the cross-section of the lumen is insonated, and for the 0.75 mm long transducer, most of the lumen within this transducer, indicated by shading 305 in FIG. 3A is filled by the crossed wavefronts from the top and bottom parts of the DGT. The unshaded portion of the lumen 306, while insonated by ultrasound, is not filled with the standing wave pattern, thus it will not discriminate against non-axial components of velocity as in the rest of the lumen. In cases where walls keep the flow lines parallel to themselves, non-axial flow will not exist. However, no doubt some non-axial flow will be detected in highly turbulent flows. Changing the beam angle and the dimensions of the DGT and non-DGT cylindrical transducers allows filling more or less of the lumen. For example, as shown in FIG. 3B where increased beam angle, increased DGT dimension 314, and reduced dimensions of the non-DGT 313, fills more of the lumen with wavefronts. If higher degrees of non-axial flow are expected, more of the lumen should be filled, and vice versa, so the optimum design for a particular situation must fit the measurement task.

According to another aspect of the present invention, the roles of DGT and non-DGT can be interchanged under the well-known general theory for wave propagation called reciprocity theorem, under which " . . . vibration by a simple source of sound of given period and intensity, the variation of pressure is the same at any point B when the source of sound is at A as it would have been at A had the source of sound been situated at B." R. T. Beyer, "Sounds of Our Times: Two Hundred Years of Acoustics," Springer-Verlag, New York 1999, page 88 (quoting Lord Rayleigh, Proc. Royal Society (London) 25, 118-122 (1876)). Also see Wikipedia http://en.wikipedia.org/wiki/Reciprocity_(electromagnetism). A well-known example of that theory is that the transmitting and receiving patterns of an antenna are the same. As can be enabled under the reciprocity theorem, without changing aforementioned structure of the transducer, non-DGT cylindrical transducer can be used to transmit ultrasound, rather than receiving it, and the cylindrical DGT can be used to receive ultrasound.

Figure 10:
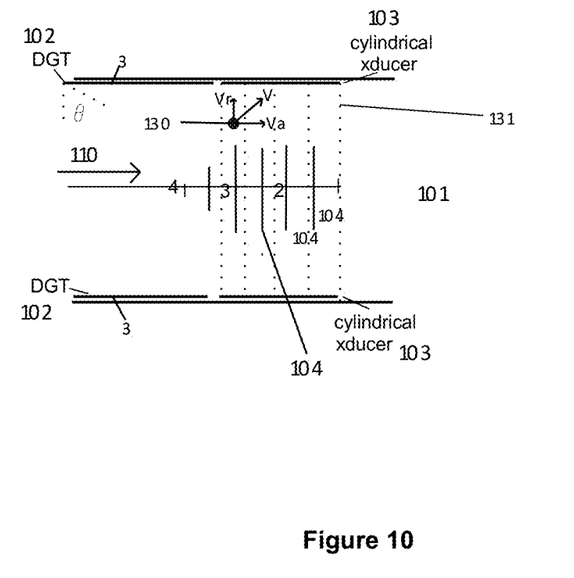
FIG. 10 shows the cross-section of the basic configuration, the combination of a cylindrical DGT with a cylindrical non-DGT transducer according to one aspect of the present invention.

With further reference to FIG. 10, it was shown that on any planes perpendicular to the axis of the cylindrical DGT, 104, the phase is the same. As this is due to the geometry and phase of the transducer elements, it is true whether transmitting or receiving. Beams 131 excited from the transmitting non-DGT are perpendicular to the transducer, whereas the receive beams of the DGT receiving the Doppler signals still form equiphase planes 104 also perpendicular to the non-DGT transducer, in the same way as illustrated in FIG. 1. If we imagine an example of a scattering particle, such as a red blood cell, shown as 130 in FIG. 10, in the "sensitive volume" of the intersection of the transmitting beams from cylindrical non-DGT and receiving cylindrical DGT, its velocity can be analyzed into two components, as shown: a radial one, Vr, in the radial direction from the axis, and an axial one, Va, along the axis. The axial component of the velocity, Va, as derived in FIG. 10, will carry a scattering center across the equiphase lines of the receive beams of the DGT; as these lines are of different phase, repeating as will be shown below every spacing d (the periodicity of the DGT), the energy scattered will produce a signal of changing phase, i.e. a Doppler signal, on the receiving cylindrical DGT. The radial component of the velocity, Vr, will carry the scattering point parallel to the equiphase planes; the scattered energy will always have the phase as the transmitting non-DGT, i.e. not have a change of phase relative to the transmitting non-DGT, therefore, produce no Doppler signal.

Embodiment 2

Figure 4:
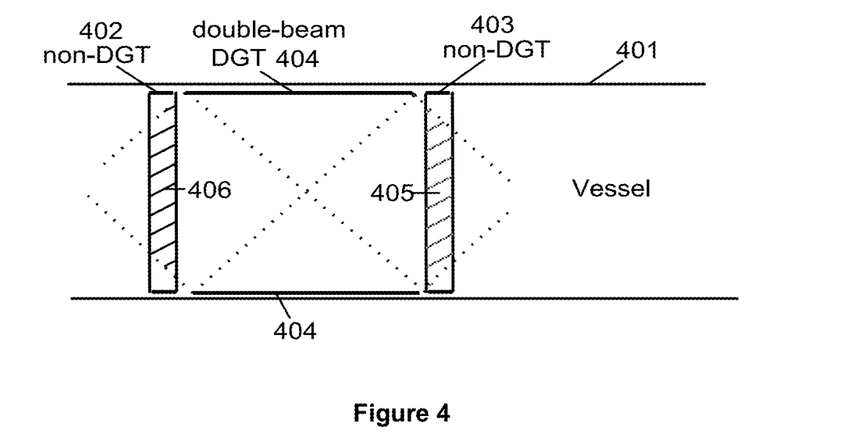
FIG. 4 shows an alternative embodiment utilizing a double-beam DGT that could be advantageous for certain conditions.

Another embodiment according to the present invention uses a double-beam DGT, as shown in FIG. 4. Two non-DGT cylindrical transducers, 402 and 403, are placed at either end of the double-beam DGT 404. Double-beam DGT has been taught in U.S. Pat. No. 5,540,230 issued to Vilkomerson and, because it requires only two elements per period d rather than 4 elements for the single beam DGT, it is easier to fabricate and connect to.

With reference to FIG. 4, at each end standing wave patterns will be set up, and Doppler signals will result from the axial components but not from the non-axial ones. The Doppler signals would be analyzed for velocity and flow by conventional CW Doppler processing means as in the previous embodiment, recognizing that the frequencies from the cylindrical transducer at one end 405 will be opposite in phase-shift direction than from that on the other end 406, i.e. a particle going left to right will produce a positive Doppler shift in 402 (as the phase is decreasing) and a negative Doppler shift in 403, as the phase is increasing. Using a single non-DGT at one end of the double-beam DGT would also be functional, but half of the acoustic energy would not be utilized for Doppler measurement in this case.

Under the reciprocal theorem, the function of DGT and non-DGT can be interchanged using the same transducer structure. However, as the single DGT transducer receives a "combined" Doppler-shifted signal, e.g. a particle going left to right produces both a positive Doppler shift signal with regard to the non-DGT transducer on the right and a negative Doppler shift signal with regard to the non-DGT signal on the left. Similarly, a particle going the opposite direction, right-to-left, will produce the same mix of Doppler-shifted signals. Therefore, to determine the direction, the two non-DGT transducers would be driven at different frequencies. Without the change in frequencies between the two non-DGT transmitters, the configuration would be symmetrical so there should be no difference between left-to-right or right-to-left.

Embodiment 3

Figure 5:
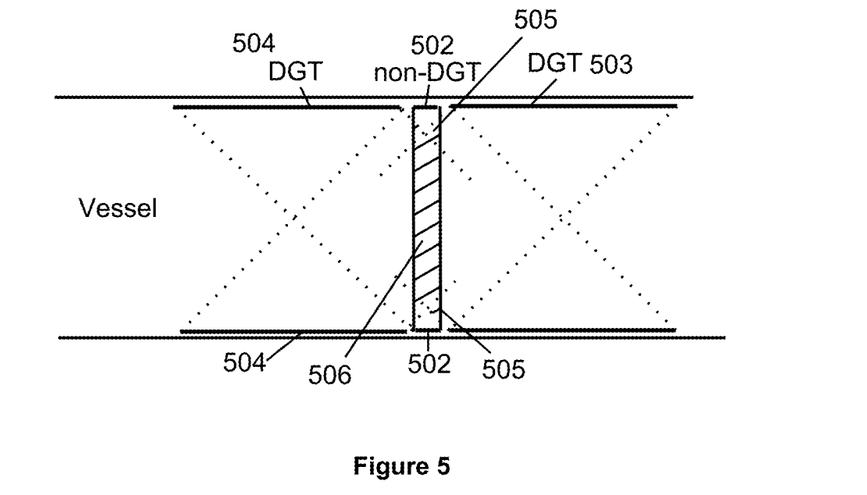
FIG. 5 shows one embodiment according to another aspect of the present invention.

With reference to FIG. 5, a single non-DGT 502 is placed between two single-beam DGT's 503 and 504 that are designed to be placed (i.e. the element spacing d) so that wavefronts of both beams cross under the non-DGT 502. In this way, a minimal amount of lumen is left unfilled by crossed-beam standing waves 505 and 506, each contributed by corresponding DGT's 503 and 504, respectively. This may be important for measuring very turbulent flow with non-axial components of flow even near the wall.

It should be noted that in the case of FIG. 5 one DGT must be driven at a different frequency than the other; otherwise, the direction of axial-moving particles interacting with one DGT's beam will not be able to be differentiated from the other direction. Another way of considering this is to recognize that this system is now symmetrical around the non-DGT, so the direction of flow cannot be determined.

Driving a DGT at different frequencies has been taught in U.S. Pat. Nos. 5,488,953 and 5,540,230, both to Vilkomerson. By driving one DGT at a different frequency, the Doppler shift from each direction is differentiated from the other by heterodyning the received signal with the appropriate driving frequencies. The Doppler shift, recovered after this heterodyning, is previously shown as v/d in magnitude; however, as the direction of flow is toward one DGT and away from the other, the Doppler shifts are of opposite sign.

Under the reciprocal theorem, the function of DGT and non-DGT can be interchanged using the same transducer structure, with the difference that the single non-DGT is driven at a single frequency. By noting on which DGT the Doppler shift is positive and which DGT the Doppler shift is negative, the direction can be ascertained (the receivers here being separate as opposed to the previous single non-DGT receiver, and so no-longer a symmetrical configuration).

Attenuating Media

The equiphase fronts used in the present invention are produced by equal strength wavefronts intersecting. In attenuating media, however, the interesting wavefronts are no longer of equal strength, but have been attenuated in their propagation through the medium. For example, in FIG. 6, which shows the embodiment of FIG. 3A or FIG. 3B, the propagation paths 603 from the center of the DGT (top and bottom), where the Doppler signals originate, to the equiphase plane at the front of the region, are equal. So in an attenuating medium they will be of equal intensity. However, the propagation distance along the path 602 is much longer than the distance along the path 601, while both paths intersect at the equiphase plane. In an attenuating medium, therefore, the wavefronts will not be of equal power as is desired to form the standing wave equiphase front. It can be seen that, other than the central point reached by propagating paths 603, the wavefronts from the top and bottom of the DGT will not be of equal strength due to greater path length through the attenuating medium. In particular, at the high frequencies required for building small and easily implanted devices, attenuation of ultrasound in blood can be significant, e.g. 11 dB/cm at 30 MHz. (Treeby B E, Zhang E Z, Thomas A, Cox B, *Measurement of the Ultrasound Attenuation and Dispersion in Whole Human Blood and Its Components from 0-70 MHz, Ultrasound in Medicine and Biology* 2011; 37:289-300.)

While it is possible to calculate the propagating path lengths from different points on the DGT, the differences in beam strength caused by the medium's attenuation can be compensated for by exciting the far "edge" of the DGT more strongly than the "near" edge. For example, in FIG. 6, the left edge of the DGT producing the 602 beam should be excited by a higher voltage than the right edge of the DGT 610 that produces the beam 601. By the symmetry of the device, driving the far edge more strongly will also equalize the wavefronts 605 and 606 that intersect at the top of the equiphase front.

In an exemplary system, Embodiment 1 was of a 30 MHz DGT measuring a 6 mm diameter vessel. The DGT was 6 mm long, and produced a beam at 45 degrees. Referring to FIG. 3A, because the cosine of 45° is 1/√2, the beam from the far edge intersects with the beam from the near edge after propagating through 6×√2=8.5 mm of blood. Using the figure of 11 dB/cm attenuation by blood at 30 MHz, and using the 8.5 mm of extra travel through the blood, we can calculate that we need to drive the far edge of the DGT with voltage 2.8 times greater than the far edge. Note that the beam from the near edge intersects with the beam from the far edge, so driving the element at the far edge 2.8 times more strongly than the element at the near edge will result in balanced beam strength at their intersection.

Figure 7:
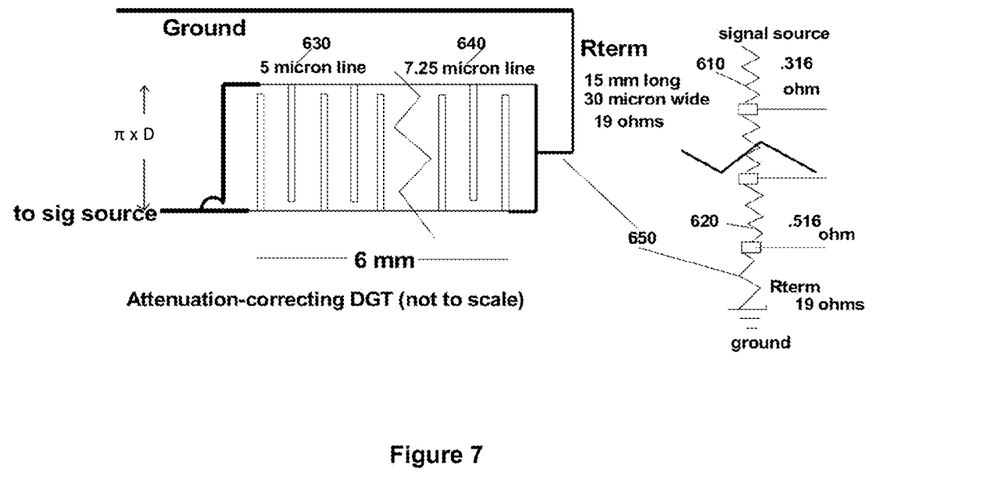
FIG. 7 shows one embodiment for the use with attenuating fluids according to another aspect of the present invention.

Note that the wavefront 603 from the center of the top-portion of the DGT intersects with the wavefront 603 from the center of the bottom DGT, with both wavefronts going the same distance from the DGT to the point of their intersection. These wavefronts have gone exactly half as far as the beam from the far edge of the DGT, or 3×√2=4.24 mm, leading to 4.67 dB, or 1.72 more attenuation than a beam from the near edge of the DGT. Similar calculations can be done for each element in the DGT. Using an exemplary resistive "ladder" as shown in FIG. 7, each element can be driven at the correct voltage to compensate for the attenuation from each element to the region of Doppler signal generation 620. Because the attenuation is logarithmically related to the propagation distance, the voltage drives are not perfectly linearly related to position but rather logarithmically related.

In another exemplary system described in Embodiment 2, using the 6 mm length DGT and double-beam at 30 MHz and 45° would require 85 pairs of elements, 15 microns wide and separated by 20.5 microns driven. By simulating the circuit, i.e. making a circuit equivalent with the capacitance of each element attached to the nodes of a resistor-in series-with-an-inductor ladder arrangement, with the other end at ground, the proper values for resistance of the interconnects connecting the nodes of the ladder can be calculated to achieve the desired variation in voltage from the far edge to the near edge.

According to one aspect of the present invention, we can form a good approximation to the needed excitations for the described DGT by controlling the width, which determines the resistance, of the interconnects between the elements of the DGT considered. With reference to FIG. 7, calculation shows that 0.316 ohms resister (610) between the first 42 elements, and 0.516 ohms resister (620) between the final 43 elements would be needed. This would correspond to gold lines 600 nm thick 5 microns wide for the first part of the array (630) and 7.25 microns wide for the second part of the array (640). An element 15.5 mm long and 30 microns wide (650) produces the value of 19 ohms needed to complete the ladder network; the total impedance of this DGT is 50.6 ohms, an appropriate value for driving with standard coax cable connections. With this configuration, it can be shown that the error in balance of the beam across the lumen is less than 2%. As excessive phase shift would also cause irregularities in the beam pattern. The total phase shift error due to the inductances in this array was less than ±5°.

The same compensation network can also be used when the roles of DGT and non-DGT are interchanged: as the elements nearest to the sensitive volume will receive the largest signal—because of the shortest path through the attenuating medium—while the elements furthest from the sensitive volume will, for the same reason, receive the smallest signal, the "signal source" for the DGT-receiving configuration, referring to FIG. 7, will be replaced by the input to the signal amplifier and the ground replaced by an open circuit, i.e. unconnected node. In this way the attenuation network, minimally attenuating the furthest element signals—for either transmit or receive—while maximally attenuating the signal from the elements nearest the cylindrical non-DGT. is the same whether the cylindrical DGT is transmitting or receiving, as it compensates for the differences in attenuation in the path lengths of the elements whether transmitting or receiving. This general approach described for compensating for the attenuation in attenuating media is only exemplary. Other methods of changing the drive voltage to compensate for attenuation or changing the attenuation as a function of position on the receiving DGT are also possible, as known to those skilled in the art.

These examples are not meant to be exhaustive but rather to indicate the different ways those skilled in the art will be able to utilize the principle of establishing planes of standing waves perpendicular to the axis to detect only axial motion, and therefore to make accurate measurement of the net flow through the vessel.

Variations of the above disclosed embodiments can also be made to accomplish the same functions. For example, with regard to Embodiment 2, a single non-DGT at one end of the double-beam DGT may be used, but half of the acoustic energy would not be utilized for Doppler measure.

Further, the non-DGT transducers used to receive the scattered ultrasound in the various embodiments can be replaced by DGT's if the spacing d' of these DGT's is different from that of the d of the insonating DGT's. As discussed in relation to FIG. 2A, the equiphase planes of a DGT with spacing d' will be d'; a particle moving along the axis, then, would produce a Doppler shift of V/d from its motion through the insonating planes produced by a DGT of periodicity d and a further Doppler shift of V/d' by passing through the receiving planes of a receiving DGT with periodicity d'.

Figure 6:
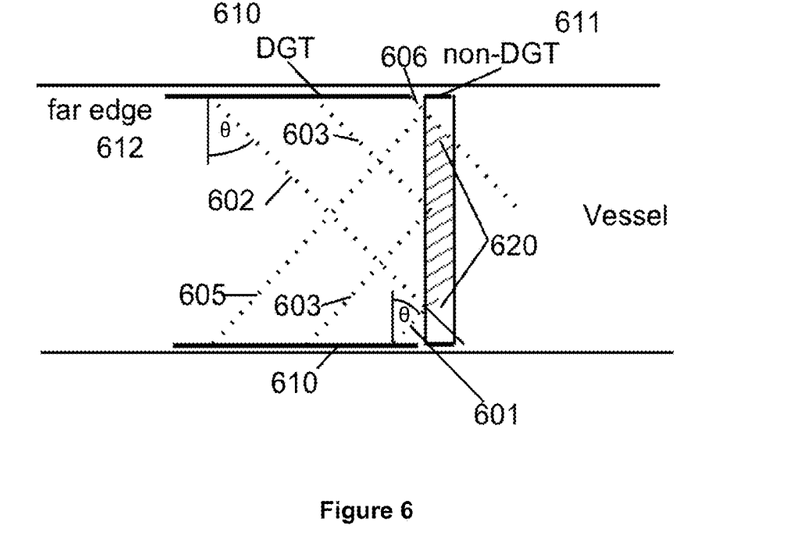
FIG. 6 shows the differing propagation paths to be considered in measuring the flow of attenuating media according to another aspect of the present invention.

For example, if a DGT was in place of the non-DGT in FIG. 6, then the Doppler shift for a particle going left to right down the axis of the vessel would be −(V/d+V/d'), producing a negative Doppler shift as the particle is moving away from both transducers.

Still further, if two DGT's replaced the two non-DGT's as receivers in FIG. 4, both would produce Doppler shift signals of (V/d−V/d'), one positive and one negative as both receivers would be producing phase planes of opposite phase progression.

Still further, the flexible film used as the subbstrate for the DGT and non-DGT structures can also be other plastics such as PET, polyethylene etc. Still further, the piezoplastic transducer material can be constructed from Nylon 7, Nylon 11 or other such piezoplastic as well as P(VDF-TrFE); and this piezoplastic layer can be spin-coated, dipped, brushed on, or in other ways formed as a layer on the film substrate.

Still further, with reference to FIG. 1, the transducer can also be wrapped outside the vessel. Further, the rotational symmetry of the transducer requires that the transducer is substantially wrapped around the lumen such that equiphase planes are perpendicular to the axis of the transducer, making it feasible for accurate measurement of velocity of fluid based on the axial component. For this purpose, the transducer is not limited to a perfect cylindrical DGT. For example, a conical shape transducer, which is wrapped around the lumen, and with a cone angle of θ (equal to the θ of sin θ=λ/d of a DGT), can be used to simulate a DGT and achieve the same results, such that the wavefronts from the angled conical surface of the conventional but conical transducer cross under the non-DGT transducer to form equiphase planes. Still further, the DGT and non-DGT do not have to be next to each other. They can be near or in a close proximity to each other, such as adjacent to, slightly apart or overlapped with each other, as long as the wavefronts from the angled ultrasound beam excited by the DGT (or as above, a conical conventional transducer), cross the region inside the non-DGT.

Still further variations, including combinations and/or alternative implementations, of the embodiments described herein can be readily obtained by one skilled in the art without burdensome and/or undue experimentation. Such variations are not to be regarded as a departure from the spirit and scope of the invention.

What is claimed is:

1. An ultrasonic transducer apparatus for receiving a signal indicative of a velocity of a fluid containing ultrasound scatterers flowing through a lumen having an axis, the apparatus comprising:
    a cylindrical non-diffraction-grating transducer adapted to be wrapped around the circumference of the lumen and coupled to a number of electrode elements for exciting an ultrasound beam perpendicular to the axis of said cylindrical non-diffraction-grating transducer;
    a cylindrical diffraction-grating transducer disposed in a close proximity to the cylindrical non-diffraction-grating transducer and coupled to a number of electrode elements, wherein said cylindrical diffraction-grating transducer is configured to be wrapped around the circumference of the lumen to form a receiving beam, wherein wavefronts of said receiving beam from opposite walls of said cylindrical diffraction-grating transducer form multiple equiphase planes perpendicular to the axis of the cylindrical diffraction-grating transducer;
    wherein the cylindrical non-diffraction-grating transducer and the cylindrical diffraction-grating transducer are configured to receive at the cylindrical diffraction-grating transducer, when the cylindrical non-diffraction-grating transducer is excited, a scattered signal corresponding to the scatterers in the fluid crossing at least one of said equiphase planes, wherein the scattered signal is indicative of a velocity of the fluid along the axis of the lumen.

2. The ultrasonic transducer apparatus of claim 1, wherein said cylindrical diffraction-grating transducer and said cylindrical non-diffraction-grating transducer comprise a flexible electroded plastic film, a piezoplastic transducer layer, and a conductor layer.

3. The ultrasonic transducer apparatus of claim 2, wherein said plastic film comprises one of a polyimide and polyethylene terephthalate (PET) material.

4. The ultrasonic transducer apparatus of claim 2, wherein said transducer layer comprises one of a poly[vinylidene-fluoride-co-trifluoroethylene] (P(VDF-TrFE)), Nylon 7, and Nylon 11 material.

5. A method of receiving a signal indicative of a velocity of a fluid containing ultrasound scatterers flowing through a lumen having an axis based on a Doppler technique, the method comprising:
    disposing a cylindrical diffraction-grating transducer in a close proximity to a cylindrical non-diffraction-grating transducer;
    exciting from said cylindrical non-diffraction-grating transducer an ultrasound beam perpendicular to the axis of the cylindrical non-diffraction-grating transducer; and
    receiving by said cylindrical diffraction-grating transducer a scattered signal indicative of a velocity of the fluid along the axis of the lumen;
    wherein said cylindrical diffraction-grating transducer and said cylindrical non-diffraction-grating transducer are configured to:
        wrap around the circumference of the lumen to form a receiving beam, wherein wavefronts of said receiving beam from opposite walls of said cylindrical diffraction-grating transducer form multiple equiphase planes perpendicular to the axis of the cylindrical diffraction-grating transducer, and
        receive the scattered signal corresponding to the scatterers in the fluid at said cylindrical diffraction-grating transducer crossing at least one of said equiphase planes.

6. The method of claim 5, further comprising compensating for attenuation of the scattered signal in the fluid by using a voltage correcting circuit.

7. The method of claim 5, wherein said cylindrical diffraction-grating transducer and said cylindrical non-diffraction-grating transducer are wrapped inside or outside the lumen.

8. The method of claim 5, wherein said cylindrical diffraction-grating transducer and said cylindrical non-diffraction-grating transducer comprise an electroded flexible plastic film, a piezoplastic transducer layer, and a conductor layer.

9. The method of claim 8, wherein said plastic film comprises one of a polyimide and PET material.

10. The method of claim 8, wherein said piezoplastic transducer layer comprises one of a P(VDF-TrFE), Nylon 7, and Nylon 11 material.

11. An ultrasonic transducer apparatus for receiving a signal indicative of a velocity of a fluid containing ultrasound scatterers flowing through a lumen having an axis, the apparatus comprising:
    a cylindrical diffraction-grating transducer;
    a first cylindrical non-diffraction-grating transducer disposed in a close proximity to one side of the cylindrical diffraction-grating transducer coupled to a number of electrode element for exciting at a first frequency a first ultrasound beam perpendicular to the axis of said first cylindrical non-diffraction-grating transducer; and
    a second cylindrical non-diffraction-grating transducer disposed in a close proximity to the opposite side of the cylindrical diffraction-grating transducer from the first cylindrical non-diffraction-grating transducer and coupled to a number of electrode element for exciting at a second frequency a second ultrasound beam perpendicular to the axis of said second cylindrical non-diffraction-grating transducer, wherein the second frequency is different from the first frequency;
    wherein said cylindrical diffraction-grating transducer is coupled to a number of electrode elements, and said first and second cylindrical non-diffraction-grating transducers and said cylindrical diffraction-grating transducer are configured to (1) form a receiving beam, wherein wavefronts of said receiving beam from opposite walls of said cylindrical diffraction-grating transducer form multiple equiphase planes perpendicular to the axis of the cylindrical diffraction-grating transducer; and (2) receive, at the cylindrical diffraction-grating transducer, the first and second cylindrical non-diffraction-grating transducers are excited, scattered signals having changing phases with respect to the first and second ultrasound beam, wherein the scattered signals correspond to the scatterers crossing at least one of the multiple equiphase planes and are indicative of a velocity of the fluid along the axis of the lumen.

12. The ultrasonic transducer apparatus of claim 11, wherein said cylindrical diffraction-grating transducer and said first and second cylindrical non-diffraction-grating transducers comprise an electroded flexible plastic film, a piezoplastic transducer layer, and a conductor layer.

13. The ultrasonic transducer apparatus of claim 12, wherein said plastic film comprises one of a polyimide, and PET material.

14. The ultrasonic transducer apparatus of claim 12, wherein said piezoplastic transducer layer comprises one of a P(VDF-TrFE), Nylon 7, and Nylon 11 material.

15. An ultrasonic transducer apparatus for receiving a signal indicative of a velocity of a scattering fluid flowing through a lumen having an axis, the apparatus comprising:
a cylindrical non-diffraction-grating transducer adapted to be wrapped around the circumference of the lumen and coupled to a number of electrode elements for exciting an ultrasound beam perpendicular to the axis of said cylindrical non-diffraction-grating transducer;
a first cylindrical diffraction-grating transducer disposed in a close proximity to one side of the cylindrical non-diffraction-grating transducer and coupled to a number of electrode elements, wherein said first cylindrical diffraction-grating transducer is configured to be wrapped around the circumference of the lumen to form a first receiving beam, wherein wavefronts of said first receiving beam from opposite walls of the first cylindrical diffraction-grating transducer form a first set of multiple equiphase planes perpendicular to the axis of the first cylindrical diffraction-grating transducer; and
a second cylindrical diffraction-grating transducer disposed in a close proximity to the opposite side of the cylindrical non-diffraction-grating transducer from the first cylindrical diffraction-grating transducer and coupled to a number of electrode elements, wherein said second cylindrical diffraction-grating transducer is configured to be wrapped around the circumference of the lumen to form a second receiving beam, wherein wavefronts of said second receiving beam from opposite walls of the second cylindrical diffraction-grating transducer form a second set of multiple equiphase planes perpendicular to the axis of the second cylindrical diffraction-grating transducer;
wherein the cylindrical non-diffraction-grating transducer and the first and second diffraction-grating transducers are configured to:
receive at the first cylindrical diffraction-grating transducers, when the cylindrical non-diffraction-grating transducer is excited, a first scattered signal corresponding to the scatters in the fluid crossing at least one of the first set of equiphase planes, wherein the first scattered signal is indicative to a velocity of the fluid along the axis of the lumen, and
receive at the second cylindrical diffraction-grating transducers, when the cylindrical non-diffraction-grating transducer is excited, a second scattered signal corresponding to the scatters in the fluid crossing at least one of the second set of equiphase planes, wherein the second scattered signal is indicative to a velocity of the fluid along the axis of the lumen.

16. The ultrasonic transducer apparatus of claim 15, wherein said first and second cylindrical diffraction-grating transducers and said cylindrical non-diffraction-grating transducers comprise a flexible plastic film, a piezoplastic transducer layer, and a conductor layer.

17. The ultrasonic transducer apparatus of claim 16, wherein said plastic film comprises one of a polyimide and PET material.

18. The ultrasonic transducer apparatus of claim 16, wherein said transducer layer comprises one of a P(VDF-TrFE), Nylon 7, and Nylon 11 material.

* * * * *